US00PP14076P29

(12) United States Plant Patent
Hanes

(10) Patent No.: US PP14,076 P2
(45) Date of Patent: Aug. 19, 2003

(54) VERBENA PLANT NAMED 'RAP PUR'

(75) Inventor: Mitchell Eugene Hanes, Morgan Hill, CA (US)

(73) Assignee: Goldsmith Seeds, Inc, Gilroy, CA (US)

( * ) Notice: Subject to any disclaimer, the term of this patent is extended or adjusted under 35 U.S.C. 154(b) by 0 days.

(21) Appl. No.: 10/092,622

(22) Filed: Mar. 8, 2002

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Annette Para
(74) *Attorney, Agent, or Firm*—Jondle & Associates PC

(57) ABSTRACT

A verbena cultivar particularly distinguished by purple colored flowers, vigorous growth and low trailing habit.

1 Drawing Sheet

GENUS AND SPECIES

Verbena hybrida×*tenuisecta*.

VARIETY DENOMINATION

'Rap Pur'.

BACKGROUND OF THE NEW PLANT

The present invention comprises a new and distinct cultivar of verbena, botanically known as Verbena hybrida× *tenuisecta*, and hereinafter referred to by the cultivar name 'Rap Pur'. The new cultivar is asexually reproduced from vegetative cuttings and tissue culture resulting from the cross of the seed/pod parent Temari Purple (PPAF), a purple commercial line×98-66-1, a purple with white eye proprietary line that is unnamed and unpatented.

'Rap Pur' is a product of a planned breeding program intended to create new verbena cultivars with purple colored flowers, dark green foliage, vigorous growth and low tailing habit.

The new cultivar was created in 1999 in Gilroy, Calif. and has been asexually reproduced repeatedly by vegetative cuttings and tissue culture in Gilroy, Calif. over a two year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new verbena plant is illustrated by the accompanying photograph which shows blooms, buds, and foliage of the plant in full color, the colors shown being as true as can be reasonably obtained by conventional photographic procedures.

The drawing shows overall plant habit and the mature inflorescence.

DESCRIPTION OF THE NEW CULTIVAR

The following detailed descriptions set forth the distinctive characteristics of 'Rap Pur'. The data which defines these characteristics were collected from asexual reproductions carried out in Gilroy, Calif. The plant history was taken on 22 week old plants grown in one gallon pots, in a double poly-greenhouse under natural light and color readings were taken in the greenhouse. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Verbena hybrida×*tenuisecta*.
*Commercial.*—Verbena.
Form: Low trailing annual, decumbent.
Growth and branching habit: Vigorous growing, moderate basal branching; low trailing habit.
Height: From soil level to top of blooms: Approximately 15–18 cm.
Width: Approximately 58–60 cm.
Time to produce a finished flowering plant: 10 weeks.
Outdoor plant performance: Typical bedding plant culture, full sun in the garden, hanging baskets or container plants.
Time to initiate roots: Approximately 4 days in the greenhouse.
Time to develop roots: Approximately 7 days in the greenhouse.
Root description: Fibrous, fleshy, white.

THE LEAVES

Length: 3.7–3.9 cm.
Width: 2.7–3.1 cm.
Leaf blade shape: Ovate.
Leaf margin: Irregular, incised-pinnatisect.
Apex aspect: Acute.
Base aspect: Cuneate.
Foliage color: Upper surface — Green RHS 137B; Lower surface is green RHS 137C.
Texture: Hispid.
Venation: Pinnate.
Venation color: Green RHS 144B.
Petiole length: 1.2–1.4 cm.
Petiole diameter: 1.5 cm.
Petiole color: Upper surface is green RHS 144B; lower surface is green RHS 144B.

THE STEM

Length: 15–28 cm.
Diameter: 2.5–3.0 cm.
Internode length: 3.5–4.0 cm.
Color: Yellow-green RHS 146B.
Texture: Hispid.
Stem anthocyanin: Some.

THE BUD

Shape: Linear.
Diameter: 0.2–0.3 cm.
Length: 1.0–1.2 cm.
Color at tight bud: Violet RHS 83C.

THE FLOWER

Blooming habit: Continuous throughout the growing season.
Inflorescence type: Spike.
Spikes per plant: 40–60 in the greenhouse.
Spike diameter: Approximately 3.7–4.5 cm.
Spike depth: Approximately 3.0–3.5 cm.
Peduncle length: 6.0–13.0 cm.
Peduncle diameter: 1.5–2.0 cm.
Peduncle color: Yellow-green RHS 143B.
Peduncle texture: Hispid and few violet colored glandular hairs.
Flower color: Upper petal surface is purple-violet RHS 80A; Lower petal surface is lavender RHS 69C.
Floret form: Salverform; sessile on spikes.
Floret (limb) diameter: Approximately 1.6–1.9 cm.
Corolla tube length: Approximately 1.6–1.8 cm.
Corolla texture: Pilose, couple of purple glandular hairs.
Number florets per spike: 24–30 (closed to fully open florets).
Number of petals: Gamopetalous, five lobed.
Petal size:
*Length of one lobe.*—0.8–0.9 cm.
*Width of one lobe.*—0.6–0.8 cm.
Petal lobe shape: Obcordate.
Petal apex shape: Emarginate.
Petal base shape: Fused.
Petal margin: Entire.
Petal texture: Papillose.
Sepals: Five sepals whose margins are fused to each other along their length with a transparent membrane of less than 1 mm in width with one smaller sepal (5 mm) attached to the base of the calyx.
Calyx length: Approximately 0.9 cm.
Calyx width: Approximately 2.0–3.0 cm.
Calyx shape: Linear.
Calyx apex: Acuminate.
Calyx color: Yellow-green RHS 143B.
Calyx texture: Hispid, with violet colored glandular hairs.
Lastingness of individual blooms: One week.
Fragrance: None.

THE REPRODUCTIVE ORGANS

Stamens: Anthers and filaments fused to upper half of corolla tube; four anthers with two pollen sacs per anther.
Pollen amount and color: Slight, yellow RHS 4A.
Pistil: One style approximately 1.6–1.8 cm; slightly recurved at the stigma.
Stigma color: Green RHS 138B.
Fruit seed set: Does not freely set seed but can produce 4 narrow nutlets, approximately 4 mm long; colored grey-brown RHS 199D and enclosed in the dried calyx.

DISEASE AND INSECT RESISTANCE

Tolerant to mildew.

COMPARISON WITH PARENTAL CULTIVARS

When the instant plant is compared to male parent 98-663-1 the 'Rap pur' plant is purple and no eye as compared to 98-663-1's rose purple with an eye. 'Rap Pur' is more mildew tolerant than 98-663-1 and 'Rap pur' has slightly broader leaves than 98-663-1.

When 'Rap pur' is compared to the female parent 'Temari purple' (PPAF) 'Rap pur' has smaller flowers and leaves than 'Temari purple'. 'Rap pur' has a more upright basal branching habit than 'Temari purple' which has a flat growing and is not very basal branching.

I claim:

1. A new and distinct cultivar of verbena plant as shown and described herein.

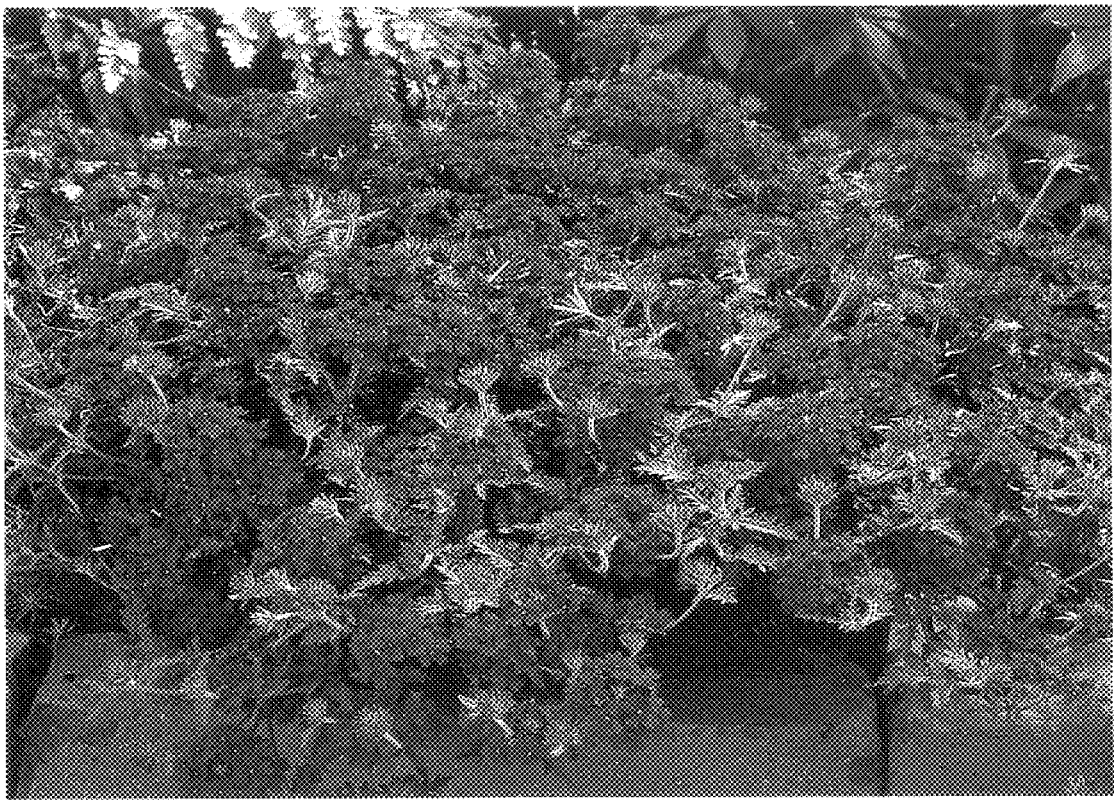

* * * * *